(12) United States Patent
Schleifenbaum et al.

(10) Patent No.: US 9,278,234 B2
(45) Date of Patent: Mar. 8, 2016

(54) ENCAPSULATED FLAVOR AND/OR FRAGRANCE PREPARATIONS

(75) Inventors: Birgit Schleifenbaum, Hoxter (DE); Jens Uhlemann, Holzminden (DE); Reinhard Boeck, Kaarst (DE); Jurgen Hinderer, Dormagen (DE)

(73) Assignee: Symrise AG, Holzminden (DE)

( * ) Notice: Subject to any disclaimer, the term of this patent is extended or adjusted under 35 U.S.C. 154(b) by 1239 days.

(21) Appl. No.: 11/774,408

(22) Filed: Jul. 6, 2007

(65) Prior Publication Data

US 2008/0015264 A1   Jan. 17, 2008

Related U.S. Application Data

(63) Continuation of application No. 10/602,409, filed on Jun. 23, 2003, now abandoned.

(51) Int. Cl.

| | |
|---|---|
| *A23L 1/22* | (2006.01) |
| *A61Q 13/00* | (2006.01) |
| *A23G 3/36* | (2006.01) |
| *A23G 4/06* | (2006.01) |
| *A23G 9/32* | (2006.01) |
| *A23L 1/064* | (2006.01) |
| *A61K 8/11* | (2006.01) |
| *A61K 8/73* | (2006.01) |
| *A61Q 11/00* | (2006.01) |
| *A61Q 19/00* | (2006.01) |
| *C11D 3/50* | (2006.01) |

(52) U.S. Cl.
CPC *A61Q 13/00* (2013.01); *A23G 3/36* (2013.01); *A23G 4/06* (2013.01); *A23G 9/32* (2013.01); *A23L 1/064* (2013.01); *A23L 1/22016* (2013.01); *A61K 8/11* (2013.01); *A61K 8/73* (2013.01); *A61K 8/732* (2013.01); *A61Q 11/00* (2013.01); *A61Q 19/00* (2013.01); *C11D 3/505* (2013.01); *A61K 2800/412* (2013.01); *A61K 2800/56* (2013.01)

(58) Field of Classification Search
USPC .............. 426/89, 96, 289, 292, 293, 534, 650
See application file for complete search history.

(56) References Cited

U.S. PATENT DOCUMENTS

| | | |
|---|---|---|
| 4,576,737 A | 3/1986 | Johnson |
| 4,946,654 A | 8/1990 | Uhlemann et al. |
| 5,004,595 A | 4/1991 | Cherukuri et al. |
| 5,094,156 A | 3/1992 | Noreille et al. |
| 5,104,799 A | 4/1992 | Mothes et al. |

FOREIGN PATENT DOCUMENTS

| | | |
|---|---|---|
| WO | WO 97/16078 | 5/1997 |
| WO | WO 98/00694 | 1/1998 |

OTHER PUBLICATIONS

Uhlemann H.: "Kontinuierliche Wirbelschicht-Spruehgranulation" Chemie.-Ingenieur. Technik DE, Verlag Chemie GMBH. Weinheim, vol. 62, No. 10, 1990, pp. 822-884, XP000176381.

*Primary Examiner* — Leslie Wong
(74) *Attorney, Agent, or Firm* — Dilworth & Barrese, LLP

(57) ABSTRACT

This invention relates to encapsulated flavor and/or fragrance preparations and a method for producing same from a spray solution consisting of an aqueous solution of polymeric carriers and emulsified flavors and/or fragrances. The granules have an adjustable particle size of between 0.2 and 2 mm, present even size distribution and a globular shape and are further characterized by a high concentration and high retention of volatile flavors.

10 Claims, No Drawings

ENCAPSULATED FLAVOR AND/OR FRAGRANCE PREPARATIONS

CROSS-REFERENCE TO RELATED APPLICATIONS

This application is a continuation of U.S. patent application Ser. No. 10/602,409, filed on Jun. 23, 2003, which is incorporated herein by reference in its entirety.

FIELD OF THE INVENTION

The present invention relates to flavoring preparations and/or perfume preparations encapsulated by continuous fluidized-bed spray agglomeration, a process for their production and their use, preferably in food.

BACKGROUND OF THE INVENTION

Flavorings and perfumes are complex liquid mixtures generally of liquid components. Flavoring granules are required for different purposes. Flavoring encapsulation via spray-drying is customary, but in this only relatively fine and irregularly structured particles are produced (R. Buttiker, Dissertation ETH Zurich No. 6148).

An alternative to spray-drying is producing flavoring granules via fluidized-bed spray agglomeration. EP A 070 719 describes, for example, the production of flavoring granules in a conventional batch-operated fluidized bed. An emulsion of the flavorings to be granulated is sprayed into a fluidized bed which consists of air-fluidized particles. The particles then act as nuclei for the formation of the granule grains.

WO 97/16078 describes the production of flavoring granules in a conventional batch-operated fluidized-bed rotor granulator. The rotor granulator generates a vortexing of the fluidized bed present therein by means of a rotating base plate. In this process material can only be sprayed onto previously introduced cores, so that the flavoring content of the final product is very low.

Both processes operate batchwise, that is to say after processing a spray-solution batch, the production process is terminated and the granules are taken out of the apparatus. A new spray solution batch must then be processed. For reasons of economic efficiency, the processes must therefore be operated with high bed contents. For preset granule growth, a corresponding amount of spray solution must be evaporated. Therefore the high bed contents lead to long residence times of the granules which are in the range of hours. However, the long residence time with simultaneous heat stress of the granules in an air steam leads to correspondingly high losses in the volatile flavorings. Reducing air temperature and/or air throughput does not decrease the flavoring loss, since then, inevitably, the time for evaporating the spray solution is extended.

A further disadvantage of the process according to EP A 070 719 is that the products it produces must be rescreened to produce narrow particle size distributions. Firstly this is an additional labor cost, secondly valuable material is lost in the course of this.

A disadvantage in WO 97/16078 is the high proportion of filler in the granule core (approximately 60 to 90% by weight) and the adsorption of the flavorings to the granules which is only at the surface. The surface adsorption reduces the protection of the flavorings, limits the maximum loading and leads to undesirably high contents of flavorings of the surface of the granules.

Although the granules produced according to EP A 070 719 or WO 97/16078 can be provided with a coating in order to adjust the solubility and flavoring-release behavior, or to achieve a specific protective action, the still relatively non-uniform particle size distribution and the relatively irregular granule surface make uniform coating with constant coating thickness difficult. An actually time- or temperature-controlled release of the flavorings or perfumes can thus not be achieved.

SUMMARY OF THE INVENTION

The purpose of the present invention is granulated encapsulated flavoring preparations and/or perfume preparations. The granules should have a settable particle size, preferably in the range from 0.2 to 2 mm, with a narrow particle size distribution and spherical geometry, and have a high loading with volatile flavorings. During production the retention of the volatile flavorings is to be able to be maximized, the screening losses are to be able to be minimized and the yield of a settable desired particle size is to be able to be maximized. The granules should, in addition, provide the ideal preconditions for coating, so that by proper choice of coating the flavoring properties can be specifically matched to an application.

Encapsulated flavoring preparations and/or perfume preparations have been found which are produced by means of continuous fluidized-bed spray agglomeration in which a flavoring preparation and/or perfume preparation is sprayed into a fluidized bed containing agglomeration nuclei and in which the mean residence time of the flavoring preparation and/or perfume preparation sprayed in is less than 20 minutes in the fluidized bed.

DETAILED DESCRIPTION OF THE INVENTION

The inventive novel flavoring preparations and/or perfume preparations fulfill the abovementioned requirements. In particular they have particle sizes of 0.2 to 2 mm, they are dust-free, the flavoring loadings are in the range from 1 to 25% by weight, the retentions of the flavorings during the agglomeration process are in the range of 60 to 90% by weight.

A process has also been found for producing encapsulated flavoring preparations and/or perfume preparations, produced by fluidized-bed spray-agglomeration, in which a flavoring preparation and/or perfume preparation is sprayed into a fluidized bed having agglomeration nuclei, characterized in that the mean residence time of the flavoring preparation and/or perfume preparation sprayed in is less than 20 minutes in the fluidized bed.

The mean residence time of the flavoring preparation and/or perfume preparation sprayed in is preferably 2 to 15 minutes, in particular 5 to 10 minutes, in the fluidized bed.

In studies it has been found that, firstly, flavorings and/or perfumes can be sufficiently granulated in a short time span of this type, and that, secondly, a product is obtained that is considerably improved with respect to the distribution of particle sizes, the geometry, the retention and loading. A high loading here means a high total amount of encapsulated flavoring based on the granule mass. The higher the retention of the individual volatile components, the lower are the losses of these components.

The inventive process can be carried out batchwise and continuously. Preferably, the inventive process is carried out continuously. A continuous process is more suitable for industrial production and has short residence times. At the same material throughput, the bed contents in the continuous processes of fluidized-bed spray agglomeration are lower than in the batchwise process. Instead of the total amount of all granule nuclei being made to grow simultaneously, in the continuous fluidized bed spray agglomeration, only a small amount of the granule nuclei are sprayed and after reaching the desired granule size they are immediately discharged via a sifter. The inventively produced encapsulated flavoring and/or perfume preparations have a small particle size distribution; in addition, the grains of the appropriate size can be specifically taken off.

In the context of the present invention, it is preferred, therefore, that the fluidized bed has a small bed height. Preferably this is 3 to 50 cm, in particular preferably 5 to 20 cm.

Continuous fluidized-bed spray agglomeration produces, from a spray solution consisting of water, emulsified flavoring and dissolved/suspended carriers, free-flowing, low-dust, grainy granules having encapsulated flavoring/perfume. In the ideal case, the basic operations of nucleus generation, drying, shaping and selective discharge of the granules which have achieved the desired particle size are performed simultaneously in one apparatus.

The fundamental principle of continuous fluidized-bed spray agglomeration (Chemie-Ingenieur-Technik, Vol. 62. (1990), pages 822 to 834) has been implemented in numerous variants. A distinction must be made, in particular, between the variants having external nucleus formation, in which nuclei are added to the bed from external sifters, grinders or other solids reservoirs, and variants having internal nucleus formation. In a comparison, the variants having external nucleus formation always have an increased residence time for two reasons:

The bed height is controlled via the nucleus supply and can therefore not be reduced below a controllable minimum.

External solids circuits are required for the process.

In the context of the present invention, therefore, processes having internal nucleus supply are preferred. One such process is, for example, the process described in EP A 163 836. This, in addition, is provided with a self-controlling mechanism for particle size control and therefore has a minimum residence time.

The spray solution can be sprayed into the fluidized bed from the bottom, from the side, but also from the top. For removing entrained solids from the exhaust air, numerous variants are possible which differ by the separation method (for example cyclone or filter) or by the position of removal (inside or outside the granulator).

Finally, for discharging the granules, preferably sifters are used. Using sifters means that only the coarse particles can leave the fluidized bed. The remaining particles remain behind in the fluidized bed until they also have achieved the desired particle size.

The granule particles are preferably, after their production, provided with a coating. This coating can be applied either in fluidized-bed apparatuses suitable therefore (top-spray coaters, bottom-spray coaters, Wurster coaters) or in film coaters. This is achieved by spraying on a solution, emulsion, dispersion or melt of a substance, which is known to be used for these purposes owing to its film-forming properties. Coating materials which can be used are substances or mixtures of substances, for example fats, waxes, proteins such as gelatin, hydrocolloids such as starches, degraded starches, chemically modified starches, modified celluloses, microcrystalline cellulose, plant exudates, such as gum arabic, ghatti gum, tragacanth, gum karaya, plant extracts such as carrageenan, guar seed meal, carob bean flour, agar, alginates, pectin, inulin, animal extracts such as chitosan and schellac, products of microorganisms such as xanthan gum, gellan gum, plastics which can be used in cosmetics or pharmaceuticals, for example polyvinylpyrrolidone, polyacrylate, polymethacrylates, polyvinylacetate phthalate, polyethylene glycol. The coating material is matched to the respective requirements of the granules, depending on the application.

The spray solution to be granulated can, similarly to the procedure in spray-drying of flavorings, consist of water having dissolved and/or suspended polymeric carriers and emulsified flavoring. The polymeric carriers can be hydrolysed or modified starches or hydrocolloids, for example gum arabic, as pure substances or in any mixing ratios.

Customary additives and ingredients such as food or cosmetic colorings, sweeteners, antioxidants, edible acids such as citric acid, flavor-enhancing substances such as sodium glutamate, vitamins, minerals, juice concentrates etc. can be added to the spray solution to be granulated.

The inventive process of fluidized-bed spray agglomeration is preferably carried out at elevated air temperatures in the range from 60° C. to 180° C., preferably from 100° C. to 140° C. The air throughput is chosen to be as great as possible for maximum drying performance. The suitable gas velocities are in the range from 0.5 to 1.5 m/s, preferably 1 m/s. The permissible product temperature is linked to the exhaust air temperature and is set via the spraying rate of the spray solution. The bed height in the procedure according to EP A 163 836 is only a few centimeters. The bed height in the variant having external nucleus formation is controlled in the range from 20 to 50 centimeters.

Suitable flavorings and perfumes are complex flavoring compositions which can comprise all individual components previously used for flavorings and perfume, that is to say flavoring and/or perfumes and essential oils or fractions thereof, but also individual flavorings or perfumes, for example acetaldehyde, menthol, ethyl butyrate, etc., or essential oils or fractions thereof.

Flavorings and perfumes which may be mentioned by way of example in the context of the present invention are preferably: berries, citrus, pome fruit, cheese, meat, fish, seafood, spices, herbs, vegetables, coffee, chocolate, mint, tobacco, wood, flowers, etc.

The inventive encapsulated flavoring preparations and/or perfume preparations can preferably be used in foods.

The invention will be described below with reference to examples.

PRODUCTION EXAMPLES

Example 1

Strawberry

In an agglomeration apparatus of the type described in EP 163 836 (having the following features: diameter of gas distributor plate: 225 mm, spray nozzle: two-component nozzle; classifying discharge: zig-zag sifter; filter: internal bag filter) a solution consisting of 44% by weight of water, 11% by weight of strawberry flavoring, 13% by weight of gum arabic and 32% by weight of hydrolysed starch (maltodextrin DE 15-19) is agglomerated. The solution is sprayed into the fluidized-bed agglomerator at a temperature of 32° C. To fluidize the bed contents, nitrogen is blown in at a rate of 140 kg/h. The inlet temperature of the fluidizing gas is 140° C. The temperature of the exhaust gas is 76° C. As classifying gas, nitrogen is also fed at a rate of 15 kg/h at a temperature of 50° C. The fluidized bed contents are approximately 1700 g. The agglomeration output is approximately 2.8 kg per hour. Free-flowing granules having a mean particle diameter of 1 mm at a bulk density of 600 g/l are obtained. The granules are round and have a smooth surface. Because of the constant pressure drop of the filter and the also constant bed contents, steady-state conditions with respect to the agglomeration process are to be assumed.

Example 2

Mint

In the apparatus described in the example "strawberry", agglomeration is carried out of a solution consisting of 37% by weight of water, 15% by weight of gum arabic, 35% by weight of hydrolysed starch (maltodextrin DE 15-19) and 13% by weight of peppermint aroma. The solution is dyed with blue dye (E131) (40 g of a 2% strength solution). The solution is sprayed into the fluidized-bed agglomerator at a temperature of 35° C. To fluidize the bed contents, nitrogen is blown in at a rate of 130 kg/h. The inlet temperature of the fluidizing gas is 140° C. The exhaust gas temperature is 85° C. The classifying gas supplied is also nitrogen at a rate of 16 kg/h at a temperature of 30° C. The contents of the fluidized bed are approximately 1700 g. The agglomeration output is approximately 4 kg per hour. Free-flowing granules having a mean particle diameter of 1 mm at a bulk density of 550 g/l are obtained. The granules are round and have a rough surface.

In the same apparatus, the previously produced granules were coated with the fat Revel A (from Loders Croklaan); 400 g were introduced in advance as a bed. By increasing the classifying gas rate to 23 kg/h at 25° C., no material is discharged, that is to say coating takes place batchwise. The melt is sprayed into the fluidized-bed agglomerator at a temperature of 74° C. The temperature of the atomizing gas is 70° C. To fluidize the bed contents, nitrogen is blown in at a rate of 100 kg/h. The inlet temperature of the cooled fluidizing gas is 16° C. The exhaust gas temperature is 28° C. Free-flowing granules are obtained. The granules are round. SEM images of the fracture surfaces show a substantially uniform coating of the granules with the fat.

Example 3

Tea Extract

In the apparatus described in the example "strawberry", a solution consisting of 25% by weight of water, 4% by weight of gum arabic, 19% by weight of hydrolysed starch (maltodextrin DE 15-19) and 52% by weight of tea extract (solids content approximately 63% by weight) is agglomerated. To fluidize the bed contents, nitrogen is blown in at a rate of 110 kg/h. The inlet temperature of the fluidizing gas is 138° C. The exhaust gas temperature is 80.5° C. The classifying gas supplied is also nitrogen at a rate of 11.5 kg/h at a temperature of 81° C. The contents of the fluidized bed are approximately 450 g. The agglomeration output is approximately 2 kg per hour. Free-flowing granules are obtained having a mean particle diameter of 0.8 mm. The granules are round and have a very smooth surface.

Example 4

Chicken

In the apparatus described in the example "strawberry", a solution consisting of 44% by weight of water, 14% by weight of gum arabic, 31% by weight of hydrolysed starch (maltodextrin DE 15-19) and 11% by weight of chicken flavoring is agglomerated. The solution is sprayed into the fluidized-bed agglomerator at a temperature of 30° C. To fluidize the bed contents, nitrogen is blown in at a rate of 130 kg/h. The inlet temperature of the fluidizing gas is 140° C. The exhaust gas temperature is 91° C. The classifying gas supplied is also nitrogen at a rate of 16 kg/h at a temperature of 65° C. The contents of the fluidized bed are approximately 650 g. The agglomeration output is approximately 2 kg per hour. Free-flowing granules are obtained having a mean particle diameter of 1.5 mm. The granules are round and have a moderately smooth surface.

Example 5

Raspberry

In the apparatus described in the example "strawberry", a solution consisting of 50% by weight of water, 11% by weight of gum arabic, 22.5% by weight of hydrolysed starch (maltodextrin DE 15-19) and 16.5% by weight of raspberry flavoring and a small amount of colouring is agglomerated. The solution is sprayed into the fluidized-bed agglomerator at a temperature of 32° C. To fluidize the bed contents, nitrogen is blown in at a rate of 110 kg/h. The inlet temperature of the fluidizing gas is 130° C. The exhaust gas temperature is 84° C. The classifying gas supplied is also nitrogen at a rate of 9 kg/h at a temperature of 81° C. The contents of the fluidized bed are approximately 300 g. The agglomeration output is approximately 1.5 kg per hour. Free-flowing granules are obtained having a mean particle diameter of 0.5 mm. The granules are round and have a moderately smooth surface (sometimes with secondary agglomerates).

In the same apparatus, the previously produced granules were coated with boysenberry flavoring (solution consisting of 50% by weight of water, 11% by weight of gum arabic, 22.5% by weight of hydrolysed starch (maltodextrin DE 15-19) and 16.5% by weight of boysenberry flavoring); 530 g are introduced in advance as a bed. By increasing the classifying gas rate to 20 kg/h at 90° C., no material is discharged, that is to say coating takes place batchwise. The solution is sprayed into the fluidized-bed agglomerator at a temperature of 26° C. The temperature of the atomizing gas is 30° C. To fluidize the bed contents, nitrogen is blown in at a rate of 110 kg/h. The inlet temperature of the fluidizing gas is 130° C. The exhaust gas temperature is 82° C. Free-flowing granules are obtained. The solid particles are round. SEM images of the fracture surfaces show a very uniform coating of the granules.

Example 6

Ethyl Butyrate

In the apparatus described in the example "strawberry", a solution consisting of 38% by weight of water, 15% by weight of gum arabic, 34% by weight of hydrolysed starch (maltodextrin DE 15-19) and 13% by weight of ethyl butyrate is agglomerated. The solution is sprayed into the fluidized-bed agglomerator at a temperature of 38° C. To fluidize the bed contents, nitrogen is blown in at a rate of 125 kg/h. The inlet temperature of the fluidizing gas is 105° C. The exhaust gas temperature is 66° C. The classifying gas supplied is also nitrogen at a rate of 10 kg/h at a temperature of 30° C. The contents of the fluidized bed are approximately 1650 g. The agglomeration output is approximately 1.4 kg per hour. Free-flowing granules are obtained having a mean particle diameter of 0.5 mm at a bulk density of 465 µl. The granules are round and have a moderately smooth surface.

Example 7

Model Flavoring Mixture

In the apparatus described in the example "strawberry", a solution consisting of 50% by weight of water, 4% by weight of gum arabic, 36% by weight of hydrolysed starch (maltodextrin DE 15-19) and 10.0% by weight of model flavoring mixture (limonene:ethyl butyrate:phenylethanol=1:1:1) is agglomerated. The solution is sprayed into the fluidized-bed agglomerator at a temperature of 22° C. To fluidize the bed contents, nitrogen is blown in at a rate of 125 kg/h. The inlet temperature of the fluidizing gas is 105° C. The exhaust gas temperature is 59° C. The classifying gas fed is also nitrogen at a rate of 14 kg/h at a temperature of 30° C. The contents of the fluidized bed are approximately 700 g. The agglomeration output is approximately 1.25 kg per hour. Free-flowing granules are obtained having a mean particle diameter of 0.7 mm. The granules are round and have a rough surface.

In the same apparatus, the previously produced granules were coated with methyl cellulose (aqueous solution containing 2.0% by weight of solid) Methocel A 15 LV (Dow Chemical); 480 g were introduced in advance as a bed. By increasing the classifying gas rate to 20 kg/h at 30° C., no material is discharged, that is to say coating takes place batchwise. The solution is sprayed into the fluidized-bed agglomerator at a temperature of 22° C. The temperature of the atomizing gas is 30° C. To fluidize the bed contents, nitrogen is blown in at a rate of 120 kg/h. The inlet temperature of the fluidizing gas is 140° C. The exhaust gas temperature is 81° C. Free-flowing granules are obtained. The solid particles are round. SEM images of the fracture surfaces show a very uniform and thin coating of the granules (5% by weight of methyl cellulose based on the weight of the granules.

Use of the Granules in the Application

The flavoring granules and perfume granules mentioned in the examples are used in the foods to be flavored (for example instant drink powders, teabags for infusion, hard and soft caramels, wine gums, bakery products, dietary preparations, compressed products, chewing gums, ice creams, ice cream coating, filled chocolate products, instant soups and instant sauces, frozen ready meals, heat-treated drinks, soups and sauces, oral hygiene products such as dental cleaning tablets and toothpastes) or are used in the cosmetics products, hygiene products, pharmaceutical products, soap products, detergent products or household products to be perfumed.

Use Examples

Example 8

Hard and Soft Caramels

Blue-dyed flavoring granules having encapsulated mint flavoring are mixed at 1% into the hot (140° C.) hard caramel mass consisting of sucrose, glucose syrup and water. The still-hot mass is then poured into moulds.

To produce soft caramels, the flavoring granules are correspondingly incorporated at 120° C. into a mass which comprises sucrose, water, glucose syrup, fat, fondant, gelatin, citric acid and an emulsifier. The mass is then cooled on a cold table to below 40° C. and aerated manually by rolling.

Advantages

By means of the noticeable particles, an optical effect can be achieved which is retained during processing and storage. Low flavoring losses occur during processing.

The flavoring is present in the matrix localized at a few places and does not migrate. As a result a particular sensory effect is achieved (hot spots). A different liquid flavoring can be added to the caramel matrix itself as a result of which a sensory double effect can be achieved.

The sucking behaviour of the hard caramels remains unchanged, the particles are not perceived as interfering.

Example 9

Jellied Fruits

Red-dyed flavoring granules having encapsulated strawberry flavoring which were additionally provided with a fat coating are incorporated at 70° C. into the mass for jellied fruits consisting of water, sucrose, glucose syrup and agar. The mass is then poured into moulding powder.

Advantages

As a result of the noticeable particles an optical effect can be achieved which is retained in the matrix during processing and storage, despite the relatively high water content.

Low flavoring losses occur during processing.

The aroma is present in the matrix localized at a few places and does not migrate. As a result a particular sensory effect is achieved (hot spots). A different liquid aroma can be added to the matrix itself, as a result of which a sensory double effect can be achieved.

Example 10

Hard Biscuits

Orange-dyed flavoring granules having encapsulated cheese aroma which was subsequently provided with a fat coating are incorporated into the dough for hard biscuits.

Advantages

Low flavoring losses occur during the baking process.

The flavoring is present in the matrix localized at a few places and does not migrate, as a result of which a particular sensory effect is achieved (hot spots). A different liquid aroma can be added into the matrix itself, as a result of which a sensory double effect can be achieved.

Example 11

Chewing Gum

Flavoring granules having encapsulated mint aroma are incorporated into chewing gum mass.

Advantages

High flavor impact due to partial localization of high flavoring concentrations in the product. The release of the flavoring takes place mechanically during chewing.

Example 12

Ice Cream

Orange-dyed flavoring granules having encapsulated apricot flavoring, which additionally comprise a fat coating, are incorporated into ice cream.

Advantages

By means of the noticeable particles an optical effect can be achieved which is retained during storage of the ice cream even under temperature fluctuations.

An additional crispness effect can be achieved even in ice cream as food having a relatively high water activity.

Example 13

Compressed Products

Flavoring granules which contain encapsulated blueberry flavoring coated with a 5% layer of methyl cellulose are added at 2% to a powder mixture of sorbitol, citric acid and aspartame and compressed on a tableting machine to form compressed products.

Advantages

The hygroscopicity of the powder mixture is markedly decreased. Sticking to the dye surfaces during compression no longer occurs.

Example 14

Comparison of the Processes

The figure shows a comparison of the different retention rates (Y axis: retention in %) of individual flavoring components from a strawberry flavoring as a function of the flavoring technique used. The vertical bars each represent the individual flavoring components arranged from left to right in order of decreasing volatility.

It may clearly be seen that in particular for the very volatile components (in each case the bars on the very left of each grouping) the retention for the inventive continuous fluidized-bed agglomeration 5 is very good. This means that the ratios of the flavoring components to one another remain virtually unchanged. The flavor profile thus substantially corresponds to that of the liquid unencapsulated flavoring.

The other techniques shown (1=absorption; 2=spray-drying; 3=agglomeration; 4=compacting) are markedly inferior to continuous fluidized-bed spray agglomeration with respect to flavor profile retention. Retention of the aroma overall is also the highest in the case of the continuous fluidized-bed spray agglomeration.

The invention claimed is:

1. Process for producing encapsulated flavoring and/or perfume preparation granules comprising:
   fluidized-bed spray agglomeration, in which a flavoring preparation and/or perfume preparation is sprayed into a fluidized bed, wherein
   the mean residence time after the flavoring preparation and/or perfumed preparation is sprayed in is less than 20 minutes in the fluidized bed;
   the flavorings and perfumes are selected from the group consisting of berries, citrus, pome fruit, cheese, meat, fish, seafood, spices, herbs, vegetables, coffee, chocolate, mint, tobacco, wood and flowers;
   the flavoring loadings are in the range from 1 to 25% by weight, and
   the retentions of the flavorings during the agglomeration process are in the range of the 60 to 90% by weight; and
   forming internal granulation nuclei in the fluidized bed during said fluidized-bed spray agglomeration step, wherein resulting encapsulated flavoring and/or perfume preparation granules comprise coated internal granulation nuclei, wherein said encapsulated flavoring and/or perfume preparation granules exiting said fluidized bed are dust-fee, wherein said fluidized-bed spray agglomeration is carried out continuously.

2. The process according to claim 1, wherein the fluidized bed has a bed-height of less than 10 cm.

3. The process according to claim 1, wherein the granules of the desired particle size are separated from the fluidized bed by sifter.

4. The process according to claim 1, wherein encapsulated flavoring and/or perfume preparation granules, after their production, are provided with an external coat by spraying a liquid coating material on the granules.

5. The process according to claim 1, wherein the flavorings and/or perfumes are used in the form of an emulsion produced by mixing the flavorings and/or perfumes with water and a polymeric carrier.

6. Process according to claim 5, wherein the polymeric carriers used is a hydrolyzed or modified starch.

7. Process according to claim 5, wherein the flavoring emulsion and/or perfume emulsion comprises as additives food dyes or cosmetic dyes, sweeteners, anti-oxidants, edible acids, flavor-enhancing substances, vitamins, minerals and/or juice concentrates.

8. The process according to claim 1, further comprising:
   retaining spray-agglomeration granules in the fluidized bed until the spray-agglomeration granules reach a desired size.

9. The process according to claim 8, wherein a zig-zag sifter is used for said retaining step.

10. The process according to claim 1, wherein said fluidized-bed process is of the internal nucleation variant, where external nuclei are not added to the fluidized-bed.

* * * * *

UNITED STATES PATENT AND TRADEMARK OFFICE
CERTIFICATE OF CORRECTION

Page 1 of 1

PATENT NO. : 9,278,234 B2
APPLICATION NO. : 11/774408
DATED : March 8, 2016
INVENTOR(S) : Birgit Schleifenbaum et al.

It is certified that error appears in the above-identified patent and that said Letters Patent is hereby corrected as shown below:

On the Title page of the printed patent, column 1, "(63) Continuation of application No. 10/602,409, filed on Jun. 23, 2003, now abandoned." should read --(63) Continuation of application No. 10/602,409, filed on Jun. 23, 2003, now abandoned, which is a continuation of application No. 09/868,297, filed on Jun. 15, 2001, now abandoned, which is a 371 of PCT/EP99/09644, filed on Dec. 8, 1999, now abandoned.

On the Title page, please insert

--(30) Foreign Application Priority Data

November 25, 1999 (DE).................................. 19956604.6
December 18, 1998 (DE).................................. 19858729.5--.

Signed and Sealed this
Twelfth Day of July, 2016

Michelle K. Lee
*Director of the United States Patent and Trademark Office*